(12) United States Patent
Jerussi

(10) Patent No.: US 6,489,341 B1
(45) Date of Patent: Dec. 3, 2002

(54) METHODS FOR THE TREATMENT OF NEUROLEPTIC AND RELATED DISORDERS USING SERTINDOLE DERIVATIVES

(75) Inventor: Thomas P. Jerussi, Framingham, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/580,492

(22) Filed: May 30, 2000

Related U.S. Application Data

(60) Provisional application No. 60/137,447, filed on Jun. 2, 1999.

(51) Int. Cl.$^7$ .................. A61K 31/454; A61K 31/4439
(52) U.S. Cl. ........................... 514/323; 514/339
(58) Field of Search ................... 514/323, 339

(56) References Cited

U.S. PATENT DOCUMENTS

| | | |
|---|---|---|
| 4,710,500 A | 12/1987 | Perregaard .................. 514/254 |
| 5,112,838 A | 5/1992 | Perregaard et al. .......... 514/323 |
| 5,238,945 A | 8/1993 | Perregaard et al. .......... 514/323 |
| 5,428,036 A | 6/1995 | Perregaard et al. ...... 514/235.2 |
| 5,439,922 A | 8/1995 | Perregaard et al. .......... 514/323 |
| 5,444,073 A | 8/1995 | Perregaard et al. .......... 514/323 |
| 5,462,948 A | 10/1995 | Perregaard et al. .......... 514/323 |
| 5,703,087 A | 12/1997 | Perregaard et al. .......... 514/278 |

FOREIGN PATENT DOCUMENTS

| | | |
|---|---|---|
| WO | 98/51685 | 11/1998 |

OTHER PUBLICATIONS

*Handbook of Pharmaceutical Excipients*, 2$^{nd}$ ed., Wade and Willer eds., pp. 257–259 (1994).
Brown, L.A., et al., *Pharmocotherapy* 18(1):69–83 (1993).
Castello, R.A., et al., *J. Pharm. Sci.* 51(2):106–108 (1962).
Drici, et al., *J. Clin. Psychopharmacology*, vol. 18, No. 6 pp 477–481 (1998).
Ereshefsky L., *J. Clin. Psychiatry* 1996; 57 (Suppl 11).
*Goodman & Gilman's The Pharmacological Basis of Therapeutics*, Hardman, J.G., et al., eds, 414–417, 856 (9$^{th}$ ed. 1996).
Janowsky, A., et al., *J. of Neurochemistry* (1986) 1272.
Marcusson, J.O., *J. Neurochemistry* (1988) 1783.
Meltzer, H.Y., *Br. J. Psychiatry* 129:23–31 (1996).
Menacherry, S.D., et al., *J. Liq. Chrom &Rel. Technol.* 20(14):2241–2257 (1997).
Moisset, Beatriz, et al., *Brian Research*, 92(1975) 157–164.
Perregaard, et al., *J. Med. Chem.* 35:1092–1101 (1992).
Perovic, S., et al., *Arzneim.–Forsch./Drug Res.* 45 (II), Nr. 11 (1995).
Remingtons: *The Practice of The Science and Pharmacy*, 19$^{th}$ ed., Gennaro, ed., p 1625 (1995).
Samara, E. et al., *Clin. Pharmacol. & Therapeutics* 59(2):187 (1996).
Samkamoto, K., et al., *Xenobiotica* 25(12):1327–1343 (1995).
Tamminga, C.A., et al., *International Clin. Psychopharmacol.* 12(suppl. 1):S29–S35 (1997).
Tejani–Butt, S.M., *J. Pharmacology and Experimental Therapeutics,* vol. 260, No. 1 (1992).
Vignon, Jacques et al., *European J. of Pharmacology,* 14S (1988) 427–436.
Wong., L.S., et al., *Pharm. Res.* 13(9):Suppl S502 (1996).
Wong, L.S., et al., *Clin. Pharmacol. Ther.* 59(2):186 (1996).
Wong, L.S., et al., *Eur. J. Clin Pharmacol* (1997) 52:223–227.
Wong., L.S., et al., *Clin. Pharmacol. Ther.* 62:157–164 (1997).

*Primary Examiner*—Phyllis G. Spivack
(74) *Attorney, Agent, or Firm*—Pennie & Edmonds, LLP

(57) ABSTRACT

The invention relates to methods of administering pharmaceutical compositions and dosage forms comprising the sertindole derivatives nor-sertindole, 5-oxo-sertindole, dehydro-sertindole, and dehydro-nor-sertindol. The methods of the invention are directed to the treatment and prevention of neuroleptic and related disorders such as, psychotic disorders, depression, anxiety, substance addiction, memory impairment and pain.

37 Claims, No Drawings

METHODS FOR THE TREATMENT OF NEUROLEPTIC AND RELATED DISORDERS USING SERTINDOLE DERIVATIVES

This application claims the benefit of provisional application No. 60/137,447, filed Jun. 2, 1999.

1. FIELD OF THE INVENTION

The invention relates to methods of using, and compositions comprising, sertindole derivatives such as nor-sertindole, 5-oxo-sertindole, dehydro-sertindole, and dehydro-nor-sertindole.

2. BACKGROUND OF THE INVENTION

Sertindole, chemically named 1-[2-[4-[5-chloro-1-(4-fluorophenyl)-1H-indol-3-yl]-1-piperidinyl]ethyl]-2-imidazolidinone, is an antipsychotic drug with high affinity for serotonin 5-HT$_2$, dopamine D$_2$ and $\alpha_1$-adrenergic receptors. Samkamoto, K., et al., *Xenobiotica* 25(12):1327–1343 (1995). Sertindole, the synthesis of which is disclosed by U.S. Pat. No. 4,710,500 and WO 98/51685, has the following structure:

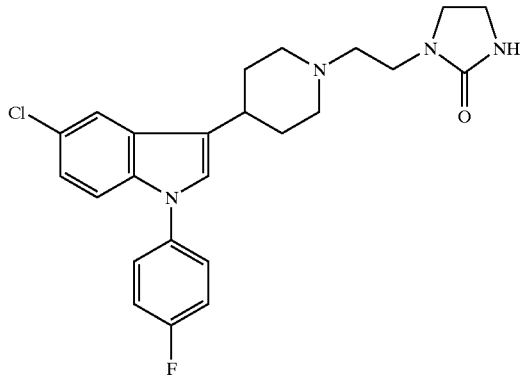

Most research directed at the therapeutic effectiveness of sertindole has focused on its use in the treatment of schizophrenia. See, e.g., U.S. Pat. No. 5,112,838; Brown, L. A., et al., *Pharmocotherapy* 18(1):69–83 (1993); Samara, E. and Granneman, R., *Clin. Pharmacol. & Therapeutics* 59(2):187 (1996); and Tamminga, C. A., et al., *International Clin. Psychopharmacol.* 12(suppl. 1):S29–S35 (1997). Some have claimed, however, that sertindole can be effective in the treatment of other disorders such as: psychosis, including drug induced psychosis (U.S. Pat. No. 5,238,945); anxiety (U.S. Pat. No. 5,439,922); memory impairment (U.S. Pat. No. 5,444,073); substance dependency (U.S. Pat. No. 5,462,948); and depression, hypertension, and extrapyramidal side effects of other antipsychotic drugs (U.S. Pat. No. 5,703,087).

The metabolism of sertindole is complex, and varies between rat, dog, monkey and human subjects, although rat and human metabolisms of the drug are reportedly similar. Samkamoto, K., et al., *Xenobiotica* 25(12):1327–1343 (1995). Analysis of the in vivo metabolism of sertindole in rats reveals that at least six metabolites are formed. Id. Three of these, 5-oxo-sertindole, nor-sertindole and dehydro-sertindole, are also formed by the human metabolism of sertindole and are shown in Scheme 1:

Scheme 1

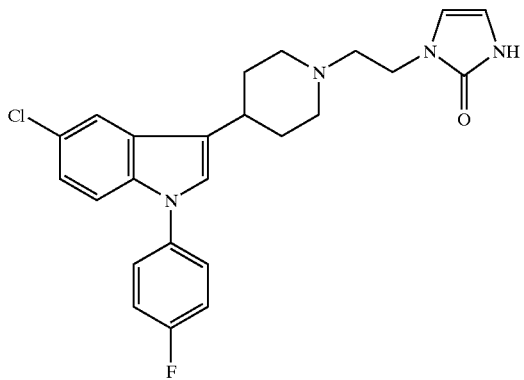

Dehydro-sertindole

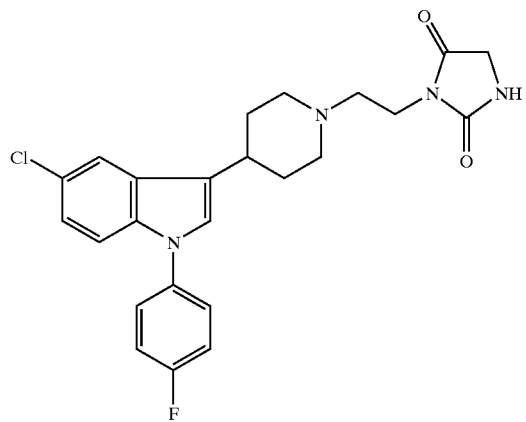

5-Oxo-sertindole

Two major human metabolites of sertindole formed after oral administration of the drug are dehydro-sertindole and nor-sertindole. Menacherry, S. D., et al., *J. Liq. Chrom. & Rel. Technol.* 20(14):2241–2257 (1997); Wong, S. L., et al., *Clin. Pharmacol. Ther.* 62:157–164 (1997).

When administered, sertindole reportedly has fewer adverse effects than antipsychotics such as haloperidol, fluphenazine and chlorpromazine. Brown, L. A., et al., *Pharmocotherapy* 18(1):69–83 (1993). This is reportedly due to the limited binding of sertindole to histaminergic, muscarinic and $\alpha_2$-adrenergic receptors, and to an unusual regional electrophysicologic characteristic of the drug. Specifically, sertindole does not induce depolarization inactivation in A9 dopamine neurons (the nigrostriatal pathway), although the drug retains activity in A10 neurons (the mesolimbic and mesocortical pathways). The mesolimbic dopamine neurons are believed to mediate antipsychotic actions of neuroleptics, while the nigrostriatal neurons are believed to mediate motor side effects. Tamminga, C. A., et al., *International Clin. Psychopharmacol.* 12(suppl. 1):S29–S35 (1997).

Despite its advantages, sertindole does cause some adverse effects when administered to humans. These are reportedly due to antagonism of the $\alpha_1$-adrenergic receptor and include, but are not limited to, nasal congestion, decreased ejaculatory volume not associated with retrograde ejaculation, loss of libido, erectile dysfunction, anorgasmia, dizziness, drymouth, tachycardia, elevation in the amounts of liver enzymes, and prolongation of the QT interval. The potentially severe consequences of QT prolongation, which include development of life-threatening cardiac (ventricular) arrhythmias such as torsades de pointes, have been of particular concern, and delayed approval of the drug by the United States Food and Drug Administration. Brown, L. A., et al., *Pharmocotherapy* 18(1):69–83 (1993).

Administration of sertindole can also cause some extrapyramidal side effects, although their severity is reportedly less than is typical of those associated with other antipsychotics such as haloperidol. Id. Extrapyramidal symptoms include acute dystonia, akathisia, parkinsonism, neuroleptic malignant syndrome, perioral tremor, and tardive dyskinesia. *Goodman & Gilman's The Pharmacological Basis of Therapeutics*, Hardman, J. G., et al., eds., 414–417 ($9^{th}$ ed. 1996).

A further disadvantage of sertindole is its potential interaction with other drugs. Sertindole interacts with a variety of isoenzyme systems, such as CYP450 2D6, 3A and 1A2, that are affected by, or aid in the metabolism of other drugs. Brown, L. A., et al., *Pharmocotherapy* 18(1):69–83 (1993). It has further been reported that a significant pharnmacodynamic interaction occurs upon concomitant administration of sertindole and other $\alpha_1$-adrenergic receptor antagonists such as prazosin. Of even greater concern are problems that can arise upon concomitant administration of sertindole and other drugs known to prolong the QT interval. Id. Examples of such drugs include, but are not limited to: methylxanthines such as theophylline; antihistimines such as terfenadine and astemizole; antibiotics such as erythromycin; antiprotozoals such as pentamidine; antipsychotics such as thioridazine; and tricyclic antidepressants. Goodman & Gilman's *The Pharmacological Basis of Therapeutics*, Hardman, J. G., et al., eds., 856 ($9^{th}$ ed. 1996).

In view of the advantages and disadvantages of sertindole, pharmaceutical compositions are desired which exhibit therapeutic benefits of sertindole, but possesses fewer of its adverse effects and/or drug interactions.

3. SUMMARY OF THE INVENTION

This invention relates to novel methods using, and pharmaceutical compositions and dosage forms comprising, sertindole derivatives such as 5-oxo-sertindole, nor-sertindole, dehydro-sertindole, and dehydro-nor-sertindole. The methods of the invention are directed to the treatment and prevention of neuroleptic and related disorders. Examples of such disorders include, but are not limited to, psychotic disorders, depression, anxiety, substance addiction, memory impairment and pain. Examples of particular types of pain include, but are not limited to, acute, chronic, somatogenic (i.e., nociceptive or neuropathic), and psychogenic.

According to the invention, the methods and compositions disclosed herein allow the treatment and prevention of neuroleptic and related disorders while reducing or avoiding adverse effects associated with sertindole. The compositions of the invention further allow the treatment and prevention of neuroleptic and related disorders while reducing or avoiding drug-drug interactions that can occur as a result of the administration of sertindole. The invention thus provides methods of treating diseases and conditions using a wide range of novel drug combinations.

Finally, the invention encompasses novel pharmaceutical compositions and/or unit dosage forms of sertindole derivatives which can be administered by oral, mucosal, parenteral, sublingual, transdermal, buccal, or topical routes.

3.1. Definitions

As used herein, the term "sertindole metabolite" means a human metabolite of sertindole, and includes, but is not limited to, nor-sertindole, 5-oxo-sertindole, and dehydro-sertindole.

As used herein, the term "sertindole derivative" means a chemical derivative of sertindole or a chemical derivative of a sertindole metabolite. Examples of sertindole derivatives include, but are not limited to, sertindole metabolites and dehydro-nor-sertindole, which has the following structure:

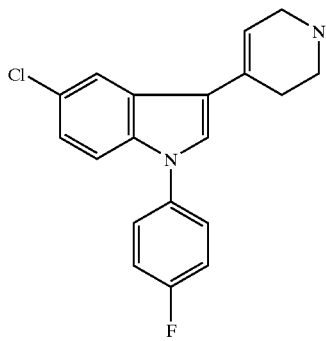

As used herein, the term "pharmaceutically acceptable salts" refers to salts prepared from pharmaceutically acceptable non-toxic organic or inorganic acids. Examples of suitable non-toxic acids include, but are not limited to, maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, 8-halotheophyllines such as 8-boromo-theophylline, hydrochloric, hydrobromic, sulfuric, sulfamic, phosphoric, nitric, alginic, anthranilic, camphorsulfonic, ethenesulfonic, formic, furoic, galacturonic, glucuronic, isethionic, maleic, malic, mucic, pamoic, pantothenic, phenylacetic, propionic, sulfanilic, tartaric, p-toluenesulfonic acid.

As used herein, the term "neuroleptic and related disorders" encompasses psychosis, depression, anxiety, substance addiction, memory impairment and pain. Other disorders known to those skilled in the art as encompassed by the term are also included. See, e.g., *Diagnostic and Statistical Manual of mental Disorders*, 4th Ed., American Psychiatric Association (1997) (DSM-IV™); and *Diagnostic and Statistical Manual of Mental Disorders*, 3rd Ed., American Psychiatric Association (1981) (DSM-III™).

As used herein, the term "psychosis" means a mental or behavioral disorder, with or without organic damage, causing gross distortion or disorganization of a person's mental capacity, affective response, capacity to recognize reality, communicate, or relate to others such that his or her capacity to cope with the ordinary demands of everyday life is diminished. Psychosis encompasses, but is not limited to, hallucinations, paranoia, affective psychosis (manic psychosis), alcoholic psychoses, arteriosclerotic psychosis, amnestic psychosis, bipolar psychosis (manic-depressive psychosis), Cheyne-Stokes psychosis, climacteric psychosis, depressive psychosis, drug psychosis, dysninesic psychosis, hysterical psychosis, infection-exhaustion psychosis, Korsakoff's psychosis, postinfectious psychosis, postpartum psychosis, posttraumatic psychosis, senile psychosis, situational psychosis, toxic psychosis, traumatic psychosis, Windigo psychosis, schizo-affective psychosis, schizophrenia and related disorders. As used herein, the terms "treatment or prevention of psychosis" and "treating or preventing psychosis" mean the relief from, or prevention of, psychological or physical symptoms of psychosis.

As used herein, the term "schizophrenia" encompasses, but is not limited to, paranoid schizophrenia, disorganized schizophrenia, catatonic schizophrenia and undifferentiated schizophrenia. Positive symptoms of schizophrenia include, but are not limited to: delusions such as delusions of persecution, reference, thought withdrawal and thought insertion; hallucinations such as auditory, visual, olfactory, gustatory and tactile hallucinations; thought disorder; and bizarre behavior. Negative, or deficit, symptoms of schizophrenia include, but are not limited to, blunted affect, poverty of speech, anhedonia and asociality. As used herein, the terms "treatment or prevention of schizophrenia" and "treating or preventing schizophrenia" mean the relief from, or prevention of, positive or negative symptoms of schizophrenia.

As used herein, the meaning of the term "depression" is consistent with its accepted meaning in the art. See, e.g., DSM-IV™ and *The Merck Manual*, Beers, M. H., et al., eds., 1531–1538 (17th ed. 1999). Psychological symptoms of depression include, but are not limited to, changes in mood, feelings of intense sadness, despair, mental slowing, loss of concentration, pessimistic worry, agitation, and self-deprecation. Physical symptoms of depression include, but are not limited to, insomnia, anorexia, weight loss, decreased energy, and abnormal hormonal circadian rhythms. As used herein, the terms "treatment or prevention of depression" and "treating or preventing depression" mean the relief from, or prevention of, psychological or physical symptoms of depression.

As used herein, the meaning of the term "anxiety" is consistent with its accepted meaning in the art. See, e.g., DSM-IV™ and *The Merck Manual*, Beers, M. H., et al., eds., 1512–1529 (17th ed. 1999). Anxiety includes, but is not limited to, anxiety attacks, free-floating anxiety, noetic anxiety, separation anxiety, and situation anxiety. Symptoms of anxiety include, but are not limited to, agitation, worry, panic, feelings of fear, helplessness or horror, and obsessive-compulsive behavior. As used herein, the terms "treatment or prevention of anxiety" and "treating or preventing anxiety" mean the relief from, or prevention of, psychological or physical symptoms of anxiety.

As used herein, the term "substance addiction" means the physical and/or psychological addiction to, or dependence on, a substance. Examples of substances to which a patient can be addicted or dependent include, but are not limited to: CNS depressants such as alcohol, barbiturates, ethchlorvynol, glutethimide, methaqualone, methyprylon and natural and synthetic opiate; anxiolytics such as alprazolam, oxazepam, temazepam, chlordiazepoxide and diazepam; stimulants such as amphetamines and methamphetamine in particular, nicotine, and cocaine; and hallucinogens such as LSD, marijuana and mescaline. Psychological symptoms of substance addiction include, but are not limited to, feelings of satisfaction and a desire to repeat the drug experience, craving of the substance, and compulsive use of the substance. Psychological symptoms of substance (i.e., drug or alcohol) withdrawal include, but are not limited to, hallucinations and the symptoms of depression and anxiety disclosed herein. Physical symptoms of substances addiction include, but are not limited to, the physical symptoms of depression defined herein. Physical symptoms of drug withdrawal include pain and the physical symptoms of depression defined herein. As used herein, the terms "treatment or prevention of substance addiction" and "treating or preventing substance addiction" mean the relief from, or prevention of, psychological or physical symptoms of substance addiction or the relief from, or prevention of, psychological or physical symptoms of substance withdrawal.

As used herein, the term "memory impairment" encompasses factual (declarative) and skillful (procedural) memory impairment such as may be associated with retrograde, anterograde, global, modality specific, transient, stable or progressive amnesias. Memory impairment can occur as a result of psychological and/or physical causes such as, but not limited to, physical trauma, Alzheimer's disease, senile dementia, cerebrovascular deficiency and Parkinson's disease. As used herein, the terms "treatment or prevention of memory impairment" and "treating or preventing memory impairment" mean the relief from, or prevention of, psychological or physical symptoms of memory impairment.

4. DETAILED DESCRIPTION OF THE INVENTION

The invention relates to methods of treating neuroleptic and related disorders using sertindole derivatives, and nor-sertindole, 5-oxo-sertindole, dehydro-sertindole, and dehydro-nor-sertindole in particular. This invention further relates to solid and liquid pharmaceutical compositions and single unit dosage forms comprising a sertindole derivative such as nor-sertindole, 5-oxo-sertindole, dehydro-sertindole, and dehydro-nor-sertindole.

Methods and compositions of the invention can be used in the treatment or prevention of disorders described herein while avoiding or reducing drug-drug interactions and other adverse effects associated with agents known for the treatment of such disorders, including sertindole. The invention encompasses compositions that further provide an improved therapeutic index over sertindole, in part because of their unique combination of dopamine, serotonin and adrenergic binding affinities.

A first embodiment of the invention encompasses a method of treating or preventing a neuroleptic or related disorder which comprises administering to a patient in need of such treatment or prevention a therapeutically effective amount of a sertindole derivative, or a pharmaceutically acceptable salt, solvate, hydrate, or clathrate thereof. Preferred sertindole derivatives include nor-sertindole, 5-oxo-sertindole, dehydro-sertindole, and dehydro-nor-sertindole. The most preferred derivative is dehydro-nor-sertindole. Neuroleptic and related disorders include, but are not limited to, psychosis, depression, anxiety, substance addiction, memory impairment and pain. Human patients suffering, or prone to suffer, from such disorders and who can thus be treated with methods of the invention include, but are not limited to: the young (i.e., males and females of less than about 14 years of age); the elderly (i.e., males and females of more than about 60 years of age) such as, but not limited to, elderly suffering from senile dementia or other age-related cognitive disorders; patients at risk of hypertension, heart failure and/or arrhythmia, such as obese patients and patients who currently or used to smoke tobacco; patients with cardiovascular disease, such as those with hypertension, histories of arrhythmias or known structural heart conditions; patients undergoing therapy for (e.g., taking medication indicated for the treatment of) high blood pressure, heart disease and/or arrhythmia; patients currently taking an $\alpha_1$-adrenergic receptor antagonist; and patients who experience, or are prone to experiencing, unacceptably severe adverse effects of sertindole.

The invention encompasses a method of treating or preventing psychosis in a patient which comprises administering to a patient in need of such treatment or prevention a therapeutically effective amount of a sertindole derivative, or a pharmaceutically acceptable salt, solvate, hydrate or clathrate thereof. The method optionally can comprise the adjunctive (e.g., concomitant) administration of a second antipsychotic agent, or a pharmaceutically acceptable salt, solvate, hydrate or clathrate thereof. Preferably, the second antipsychotic is an atypical antipsycotic (i.e., an antipsychotic that produces less extrapyramidal side effects than typical antipsychotics or neuroleptics; see, e.g. Meltzer, H. Y., *Br. J. Psychiatry* 129:23–31 (1996)). A preferred second antipsychotic agent is mirtazapine. Specific psychosis which may be treated or prevented according to this method include, but are not limited to, hallucinations, paranoia, affective psychosis (manic psychosis), alcoholic psychoses, arteriosclerotic psychosis, amnestic psychosis, bipolar psychosis (manic-depressive psychosis), Cheyne-Stokes psychosis, climacteric psychosis, depressive psychosis, drug psychosis, dysmnesic psychosis, hysterical psychosis, infection-exhaustion psychosis, Korsakoff's psychosis, postinfectious psychosis, postpartum psychosis, posttraumatic psychosis, senile psychosis, situational psychosis, toxic psychosis, traumatic psychosis, Windigo psychosis, schizo-affective psychosis and schizophrenia.

The invention thus encompasses a method of treating or preventing schizophrenia in a patient which comprises administering to a patient in need of such treatment or prevention a therapeutically effective amount of a sertindole derivative, or a pharmaceutically acceptable salt, solvate, hydrate, or clathrate thereof. This embodiment encompasses methods of treating and preventing paranoid schizophrenia, disorganized schizophrenia, catatonic schizophrenia and undifferentiated schizophrenia.

The invention also encompasses a method of treating or preventing depression in a patient which comprises administering to a patient in need of such treatment or prevention a therapeutically effective amount of a sertindole derivative, or a pharmaceutically acceptable salt, solvate, hydrate, or clathrate thereof.

The invention also encompasses a method of treating or preventing anxiety in a patient which comprises administering to a patient in need of such treatment or prevention a therapeutically effective amount of a sertindole derivative, or a pharmaceutically acceptable salt, solvate, hydrate, or clathrate thereof. This embodiment encompasses methods of treating and preventing anxiety attacks, free-floating anxiety, noetic anxiety, separation anxiety, and situation anxiety.

The invention also encompasses a method of treating or preventing substance addiction in a patient which comprises administering to a patient in need of such treatment or prevention a therapeutically effective amount of a sertindole derivative, or a pharmaceutically acceptable salt, solvate, hydrate, or clathrate thereof This embodiment encompasses a method of treating substance addition in patient addicted to a substance. This embodiment further encompasses a method of preventing substance addiction in a patient to whom a potentially addictive substance is to be administered. This embodiment also encompasses a method of treating a patient who was addicted to a substance.

The invention also encompasses a method of treating or preventing memory impairment in a patient which comprises administering to a patient in need of such treatment or prevention a therapeutically effective amount of a sertindole derivative, or a pharmaceutically acceptable salt, solvate, hydrate, or clathrate thereof.

The invention also encompasses a method of treating or preventing pain in a patient which comprises administering to a patient in need of such treatment or prevention a therapeutically effective amount of a sertindole derivative, or a pharmaceutically acceptable salt, solvate, hydrate, or clathrate thereof. Particular types of pain which may be treated or prevented according to this method include, but are not limited to, acute, chronic, somatogenic (i.e., nociceptive or neuropathic), and psychogenic pain. This method optionally can further comprise the adjunctive (e.g., concomitant) administration of an additional therapeutic agent. Examples of additional therapeutic agents include, but are not limited to: opiate analgesics; non-opiate analgesics; analgesics and antipyretics; nonsteroidal anti-inflammatory drugs; tricyclic antidepressants such as desipramine, imipramine, amytriptiline, and nortriptile; anticonvulsants such as carbamazepine and valproate; serotonin reuptake inhibitors such as fluoxetine, paraoxetine, sertraline, and methysergide; mixed serotonin-norepinephrine reuptake inhibitors such as venlafaxine and duloxetine; serotonin receptor agonists; cholinergenic (muscarinic and nicotinic) analgesics such as ketoprofen, aspirin, acetominophen, indomethacin, ketorolac, and methotrimeprazine; adrenergic agents; neurokinin antagonists; xanthine oxidase inhibitors such as allopurinol; and pharmaceutically acceptable salts, solvates, hydrates and clathrates thereof.

A second embodiment of the invention encompasses pharmaceutical compositions comprising a sertindole derivative, or a pharmaceutically acceptable salt, solvate, hydrate, or clathrate thereof. Preferred sertindole derivatives include nor-sertindole, 5-oxo-sertindole, dehydro-sertindole, and dehydro-nor-sertindole. The most preferred derivative is dehydro-nor-sertindole. This embodiment further encompasses individual dosage forms of sertindole derivatives, or pharmaceutically acceptable salts, solvates, hydrates, or clathrates thereof. Individual dosage forms of the invention can be suitable for oral, mucosal (including rectal, nasal, or vaginal), parenteral (including subcutaneous, intramuscular, bolus injection, intraarterial, or intravenous), sublingual, transdermal, buccal, or topical administration.

Certain pharmaceutical compositions and dosage forms encompassed by this embodiment comprise a sertindole derivative, or a pharmaceutically acceptable salt, solvate, hydrate, or clathrate thereof, and a second antipsychotic agent. Preferably, the second antipsychotic is an atypical antipsycotic (i.e., an antipsychotic that produces less extrapyramidal side effects than typical antipsychotics or neuroleptics; see, e.g., Meltzer, H. Y., *Br. J. Psychiatry* 129:23–31 (1996)). These pharmaceutical compositions and dosage forms are useful in the treatment of psychosis.

Additional pharmaceutical compositions and dosage forms encompassed by this embodiment comprises a sertindole derivative, or a pharmaceutically acceptable salt, solvate, hydrate, or clathrate thereof, and an additional therapeutic agent. Examples of additional therapeutic agents include, but are not limited to: opiate analgesics; non-opiate analgesics; analgesics and antipyretics; nonsteroidal anti-inflammatory drugs; tricyclic antidepressants such as desipramine, imipramine, amytriptiline, and nortriptile; anticonvulsants such as carbamazepine and valproate; serotonin reuptake inhibitors such as fluoxetine, paraoxetine, sertraline, and methysergide; mixed serotonin-norepinephrine reuptake inhibitors such as venlafaxine and duloxetine; serotonin receptor agonists; cholinergenic (muscarinic and nicotinic) analgesics such as ketoprofen, aspirin, acetominophen, indomethacin, ketorolac, and methotrimeprazine; adrenergic agents; neurokinin antagonists; xanthine oxidase inhibitors such as allopurinol; and pharmaceutically acceptable salts, solvates, hydrates and clathrates thereof. These pharmaceutical compositions and dosage forms are useful in the treatment of pain.

4.1. Synthesis and Preparation

Sertindole derivatives of the invention are readily prepared and purified by methods known to those skilled in the art. For example, preferred methods of preparing nor-sertindole are disclosed by Perregaard, et al., *J. Med. Chem.* 35:1092–1101 (1992), U.S. Pat. No. 4,710,500 and WO 98/51685, all of which are incorporated herein by reference. One method of preparing nor-sertindole comprises the reaction of 1-(4-fluorophenyl)-5-chlorindole and 4-piperidone-monohydrate-hydrochloride as shown in Scheme 2:

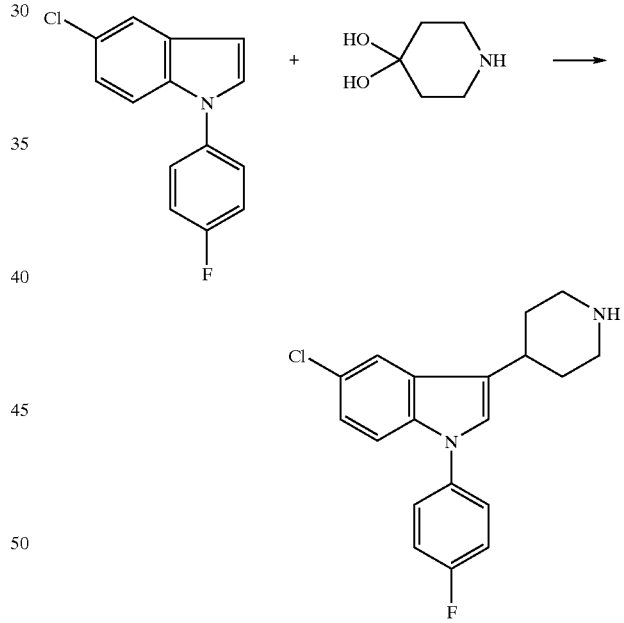

Scheme 2 wherein the reaction conditions are known to those skilled in the art and described by WO 98/51685.

Alternatively, nor-sertindole can be prepared from sertindole itself by cleaving the piperidinyl-ethyl bond. Suitable methods of bond cleavage are known to those skilled in the art. See, e.g., March, J., *Advanced Organic Chemistry* 436–437 (4$^{th}$ ed. 1992).

The sertindole derivative dehydro-nor-sertindole can be prepared in a manner analogous to that shown in Scheme 2 above, wherein 1-(4-fluorophenyl)-5-chlorindole is reacted with a compound of the formula:

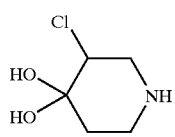

The reaction product is subsequently converted to dehydro-nor-sertindole via a dehydrohalogenation reaction under conditions known to those skilled in the art. See, e.g., March, J., *Advanced Organic Chemistry* 1023–1025 (4th ed. 1992).

Preferred methods of preparing 5-oxo-sertindole and dehydro-sertindole are disclosed by U.S. Pat. No. 5,703,087 and WO 98/51685, both of which are incorporated herein by reference. For example, 5-oxo-sertindole and dehydro-sertindole can be prepared by reacting nor-sertindole with compounds of the formulas:

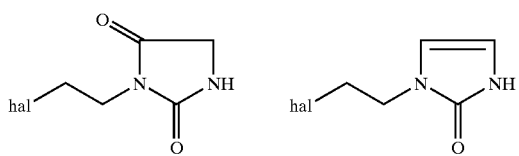

wherein hal is chloro, bromo or iodo. Suitable reaction conditions are known to those skilled in the art, and include those disclosed by U.S. Pat. No. 5,703,087.

The 5-oxo-sertindole and dehydro-sertindole derivatives can also be prepared according to the reaction shown in Scheme 3:

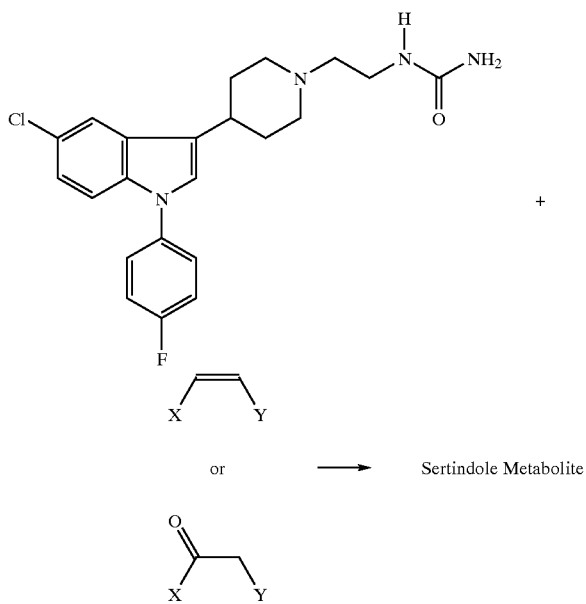

wherein X and Y are independently chloro, bromo or iodo. Suitable reaction conditions are known to those skilled in the art, and include those disclosed by U.S. Pat. No. 5,703,087. Synthesis of the amide is described in detail below.

Alternatively, 5-oxo-sertindole and dehydro-sertindole can be prepared from sertindole itself by oxidation of the imidazolidinone moiety. Suitable oxidation conditions are known to those skilled in the art. See, e.g., March, J., *Advanced Organic Chemistry* 1158–1205 (4th ed. 1992).

4.2. Pharmaceutical Compositions and Method of Use

The active compounds of the invention (i.e., sertindole derivatives and optionally at least one additional antipsychotic and/or therapeutic agent) can be used in the treatment or prevention of a wide range of neuroleptic and related disorders. The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range of sertindole derivative for the conditions (i.e., disorders) described herein lie within the range of from about 0.1 mg to about 1000 mg per day, given as a single once-a-day dose in the morning but preferably as divided doses throughout the day. More preferably, the daily dose is administered twice daily in equally divided doses. Preferably, a daily dose range should be from about 5 mg to about 500 mg per day, more preferably, from about 10 mg to about 200 mg per day. In managing the patient, the therapy should be initiated at a lower dose, perhaps from about 1 mg to about 25 mg, and increased if necessary up to from about 200 mg to about 1000 mg per day as either a single dose or divided doses, depending on the patient's global response.

It may be necessary to use dosages of a sertindole derivative outside the ranges disclosed herein in some cases, as will be apparent to those of ordinary skill in the art. Although elimination of sertindole derivatives from the bloodstream reportedly exhibits little dependency on renal function (see, e.g., Wong, S. L., et al., *Eur J. Clin. Pharmacol.* 52:223–227 (1997)), it is still recommended that the dosage of sertindole derivative be reduced by 25% in patients with mild to moderate renal impairment, and upward titrated if safe to do so. It is further recommended that the total daily dose of sertindole derivative be reduced by at least 50% in patients with moderate hepatic impairment. For patients undergoing hemodialysis, it is recommended that the total daily dose be reduced by 5% and that the dose be withheld until the dialysis treatment is completed. Furthermore, it is noted that the clinician or treating physician will know how and when to interrupt, adjust, or terminate therapy in conjunction with individual patient response.

The elimination of sertindole derivatives from the bloodstream of elderly male and female patients reportedly differs little from that observed in young patients. Wong, S. L., et al., *Clin. Pharmacol. Ther.* 52:157–164 (1997). It is still recommended, however, that when administered to elderly patients, the compounds disclosed herein are initially administered in low doses (e.g., reduced by about 25%).

Lower initial doses of sertindole derivative are also suggested when a sertindole derivative is adjunctively administered with another active ingredient, such as one of the antipsychotics or therapeutic agents described above. Additional active ingredients, in particular those described herein, can provide an enhancing or synergistic effect when adjunctively administered with a sertindole derivative. As will be recognized by the clinician or treating physician, such an effect may require adjustment of the sertindole derivative dose amount and/or dose frequency depending on the condition being prevented or treated.

The phrase "therapeutically effective amount," as used herein with respect to the treatment or prevention of neuroleptic and related disorders encompasses the above described dosage amounts and dose frequency schedules. Different therapeutically effective amounts may be applicable for different diseases and conditions, as will be readily known by those of ordinary skill in the art. Similarly, amounts sufficient to treat or prevent such disorders, but insufficient to cause, or sufficient to reduce, adverse effects associated with sertindole, are also encompassed by the above described dosage amounts and dose frequency schedules.

Any suitable route of administration can be employed for providing the patient with an effective dosage of a sertindole derivative. For example, oral, mucosal (including rectal), parenteral (including subcutaneous, intramuscular, bolus injection, and intravenous), sublingual, transdermal, nasal, and buccal routes can be employed. In the acute treatment or management of a disease or condition, it is preferred that the active ingredient be administered orally. In the acute treatment or management of a disease or condition, it is preferred that the active ingredient be administered parenterally.

The pharmaceutical compositions of the invention comprise at least one sertindole derivative, or a pharmaceutically acceptable salt, solvate, hydrate, or clathrate thereof as an active ingredient, optionally at least one additional active ingredient, and optionally an inactive (e.g., a pharmaceutically acceptable carrier). The pharmaceutical compositions can be solid or liquid.

Compositions of the invention are suitable for oral, mucosal (including rectal), parenteral (including subcutaneous, intramuscular, bolus injection, and intravenous), sublingual, transdermal, nasal, or buccal administration, although the most suitable route in any given case will depend on the nature and severity of the condition being treated. The compositions can be conveniently presented in unit dosage form and prepared by any of the methods well known in the part of pharmacy. Dosage forms include tablets, caplets, troches, lozenges, dispersions, suspensions, suppositories, solutions, capsules, soft elastic gelatin capsules, patches, and the like. Preferred dosage forms are suitable for oral administration. Lyophilized dosage forms can be orally administered, or can be reconstituted to provide sterile, liquid dosage forms suitable for parenteral administration to a patient.

In practical use, a sertindole derivative can be combined as the active ingredient in intimate admixture with a pharmaceutically acceptable carrier according to conventional pharmaceutical compounding techniques. The carrier can take a wide variety of forms and comprises a number of components depending on the form of preparation desired for administration. The compositions of the invention include, but are not limited to, suspensions, solutions and elixirs; aerosols; or excipients, including, but not limited to, starches, sugars, microcrystalline cellulose, diluents, granulating agents, lubricants, binders, disintegrating agents, and the like. Preferably, the pharmaceutical composition is in the form of an oral preparation.

Pharmaceutical compositions of the invention suitable for oral administration can be presented as discrete pharmaceutical unit dosage forms, such as capsules, cachets, soft elastic gelatin capsules, tablets, caplets, or aerosols sprays, each containing a predetermined amount of the active ingredients, as a powder or granules, or as a solution or a suspension in an aqueous liquid, a non-aqueous liquid, an oil-in-water emulsion, or a water-in-oil liquid emulsion. Such compositions can be prepared by any method known in the art of pharmacy which comprises the step of bringing an active ingredient into association with a carrier. In general, the compositions are prepared by uniformly and intimately admixing the active ingredients with liquid carriers or finely divided solid carriers or both, and then, if necessary, shaping the product into the desired presentation. Oral solid preparations are preferred over oral liquid preparations. Preferred oral solid preparations are capsules and tablets.

A tablet can be prepared by compression or molding techniques. Compressed tablets can be prepared by compressing in a suitable machine the active ingredient(s) in a free-flowing form, such as powder or granules, optionally mixed with a binder, lubricant, inert diluent, granulating agent, surface active or dispersing agent, or the like. Molded tablets can be made by molding, in a suitable machine, a mixture of the powdered compound moistened with an inert liquid diluent. Preferably, each tablet, cachet, caplet, or capsule contains from about 1 mg to about 1000 mg of sertindole derivative, more preferably from about 5 mg to about 500 mg, and most preferably from about 10 mg to about 200 mg.

Pharmaceutical compositions of the invention can also be formulated as a pharmaceutical composition in a soft elastic gelatin capsule unit dosage form by using conventional methods well known in the art. See, e.g., Ebert, *Pharm. Tech.* 1(5):44–50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell can be changed by varying the type of gelatin used and the amounts of plasticizer and water. The soft gelatin shells can contain a preservative, such as methyl- and propylparabens and sorbic acid, to prevent the growth of fungi. The active ingredient can be dissolved or suspended in a liquid vehicle or carrier, such as vegetable or mineral oils, glycols, such as polyethylene glycol and propylene glycol, triglycerides, surfactants, such as polysorbates, or a combination thereof.

A pharmaceutically acceptable excipient used in the compositions and dosage form of the invention can be a binder, a filler, a mixture thereof. A pharmaceutically acceptable excipient can also include a lubricant, a disintegrant, or mixtures thereof. Preferred excipients are lactose, croscarmellose, microcrystalline cellulose, pre-gelatinized starch, and magnesium stearate. One embodiment of the invention encompasses a pharmaceutical composition which is substantially free of all mono- or di-saccharide excipients. Another embodiment of the invention encompasses a lactose-free pharmaceutical composition.

Binders suitable for use in the compositions and dosage forms of the invention include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose or mixtures thereof.

Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., U.S.A.). An exemplary suitable binder is a mixture of microcrystalline cellulose and sodium carboxymethyl cellulose sold as AVICEL RC-581 by FMC Corporation.

Fillers suitable for use in the compositions and dosage forms of the invention include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, or mixtures thereof.

The binder/filler in pharmaceutical compositions of the invention is typically present in about 50 to about 99 weight percent of the pharmaceutical composition.

Disintegrants are used to cause the tablet to disintegrate when exposed to an aqueous environment. Too much of a disintegrant will produce tablets which may disintegrate in the bottle due to atmospheric moisture; too little may be insufficient for disintegration to occur and may thus alter the rate and extent of release of the drug ingredient(s) from the dosage form. Thus, a sufficient amount of disintegrant that is neither too little nor too much to detrimentally alter the release of the drug ingredient(s) should be used to form dosage forms of sertindole derivative made according to the invention. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, can be used in the pharmaceutical composition.

Disintegrants suitable for use in the compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants suitable for use in the compositions and dosage forms of the invention include, but are not limited to, calcium stearate, magnesium stearate, mineral oil, light mineral oil, glycerin, sorbitol, mannitol, polyethylene glycol, other glycois, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, or mixtures thereof. Additional lubricants include, for example, a syloid silica gel (AEROSIL 200, manufactured by W. R. Grace Co. of Baltimore Md.), a coagulated aerosol of synthetic silica (marketed by Deaussa Co. of Plano, Tex.), CAB-O-SIL (a pyrogenic silicon dioxide product sold by Cabot Co. of Boston, Mass.), or mixtures thereof. A lubricant can optionally be added, typically in an amount of less than about 1 weight percent of the pharmaceutical composition.

In addition to the common dosage forms set out above, the compounds of the invention can also be administered by controlled release means or delivery devices that are well known to those of ordinary skill in the art, such as those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, the disclosures of which are each incorporated herein by express reference thereto. These pharmaceutical compositions can be used to provide slow or controlled-release of one or more of the active ingredients therein using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, caplets, and the like, that are adapted for controlled-release are encompassed by the invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; 3) increased patient compliance; and 4) a lower peak plasma concentration of the drug. The latter advantage is significant because high peak plasma concentrations of some drugs can cause adverse effects not associated with lower, but still therapeutically effective, plasma concentrations.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

The controlled-release of an active ingredient can be stimulated by various inducers, for example pH, temperature, enzymes, water, or other physiological conditions or compounds. The term "controlled-release component" in the context of the invention is defined herein as a compound or compounds, including, but not limited to, polymers, polymer matrices, gels, permeable membranes, liposomes, microspheres, or the like, or a combination thereof, that facilitates the controlled-release of the active ingredient.

Pharmaceutical compositions of the invention can also be formulated for parenteral administration by injection (subcutaneous, bolus injection, intramuscular, or intravenous), and can be dispensed in a unit dosage form, such as a multidose container or an ampule. Such compositions for parenteral administration can be in the form of suspensions, solutions, emulsions, or the like in aqueous or oily vehicles, and in addition to the active ingredients can contain one or more formulary agents, such as dispersing agents, suspending agents, stabilizing agents, preservatives, and the like.

The invention is further defined by reference to the following examples describing in detail the preparation of the compositions of the invention. It will be apparent to those skilled in the art that many modifications, both to materials and methods, may be practiced without departing from the purpose and interest of this invention.

5. EXAMPLES

5.1. Example 1

Synthesis of Nor-Sertindole

Preparation of 1-(4-fluorophenyl)-3-acetoxy-5-chloroindole N-(4-fluorophenyl)-N-(2-carboxyphenyl)glycin (717.1 g, 2.22 mol) prepared according to WO 98/51685, sodium acetate (36.4 g, 0.44 mol, 0.2 eq.) and acetic anhydride are placed in a 4 L three necked flask equipped with mechanical stirrer and reflux condenser.

The suspension is heated while stirring under relux. The reaction mixture is reluxed for one hour and then cooled to room temperature on ice/water bath. The homogenous suspension is poured while stirring onto ice (2 L) and then neutralized with concentrated NaOH (approximately 6 L) until a pH of 6–7 is reached. During the neutralization, the temperature is kept under about 30° C., which can require the addition of more ice. The precipitated product is isolated by filtration. The product is then washed with 3 L water and 2 L of n-heptane, and dried overnight under vacuum and at a temperature of about 60° C. Approximate yield is 600 grams.

Preparation of 1-(4-fluorophenyl)-5-chlorindole 1-(4-fluorophenyl)-3-acetoxy-5-chloroindole (100.0 g, 0.33 mol) is dissolved in 1000 ml ethanol. Over the course of the next hour, sodium borohydride pellets (18.7 g, 1.5 eq.) are added batchwise at reflux. The reaction mixture is stirred over night at reflux, and cooled to room temperature. Concentrated HCl (approximately 50 ml) are added until a pH of 1 is reached. The reaction mixture is stirred at room temperature for about one hour. 200 ml demineralized water is added, and the resulting suspension is filtered. The filter cake is washed with about 50 ml water and about 10 ml ethanol. The resulting product is dried overnight under vacuum at a temperature of about 50° C. Approximate yield is 68 grams.

Preparation of 5-chloro- 1 -(4-fluorophenyl)-3-(1,2,3 6-tetrahydropvridin-4-yl)indole 1-(4-fluorophenyl)-5-chlorindole (6.7 kg) and 4-piperidone-mono-hydrate hydrochloride (8.38 kg) are transferred to a 200 L reactor under $N_2$ cover. Acetic acid (67 L) is added and the reaction mixture is heated to 60° C. Concentrated HCI (37%, 33.5 L) is added during one-half hour and the resulting mixture is heated to reflux (85° C.), and refluxed for one hour, reaching a final temperature of 95° C. After cooling to 30° C., 33.5 L acetone are added followed by further cooling to 25° C. Filtration, wash (actone 20 L) and drying under vacuum at 60° C. yields about 8.9 kg of the title product (nor-sertinodole).

5.2. Example 2

Synthesis of 5-Oxo-Sertindole

Preparation of 1-(2-chloroethyl)imidazolidin-2,5-dione

To a suspension of glycine (49 g) in water (750 ml) is added sodium hydroxide (39 g). The mixture is cooled to 0° C. 2-Chloroethylisocyanate (75 g) is added dropwise at 0° C. to 10° C. over one-half hour. The mixture is stirred for another hour at 10° C., and the pH is adjusted to 1 by addition of concentrated HCl. The precipitated glycine derivative is filtered off, washed with water and finally dried under vacuum. Approximate yield is 106 g. All of the glycine derivative thus obtained is suspended in concentrated HCl (520 ml) and heated to reflux for 20 minutes. The acidic solvent is evaporated under vacuum. The remaining crude product is dissolved in dichloromethane and dried (annhydrous $MgSO_4$). The dichloromethane is evaporated, and the crystalline product is recrystallized from ethyl acetate to yield about 62 g of the title compound.

Preparation of 1-[2-[4-[5-chloro-1-(4-fluorophenyl)-1H-indol-3-yl]piperidin-1-yl]ethyl]midazolidin-2,5-dione A suspension of 5-chloro-1-(4-fluorophenyl)-3-(1,2,3,6-tetrahydropyridin-4-yl)indole (45 g) prepared according to Example 1, 1-(2-chloroethyl)imidazolidin-2,5, dione (45 g), potassium carbonate (40 g) and potassium iodide (10 g) is refluxed for 5 hours in methyl isobutyl ketone (MIBK) (400 ml). The mixture is filtered while hot, and MIBK is subsequetnly evaproated under vacuum. The remaining crude product is purified by column chromatography on silica gel using a mixture of ethyl acetate/ethanol/triethylamine (90:10:4) as eluent. The product is recrystallized from ethyl acetate to yield approximately 21 g of 5-oxo-sertindole.

5.3. Example 3

Synthesis of Dehydro-Sertindole

Preparation of 5-chloro-1-(4-fluorophenyl)-3-[1-(2-ureidoethyl)piperidin-4yl]-1H-indol Potassium cyanate (4.9 g) is suspended in dichloromethane (50 ml) followed by dropwise addition of trifluoroacetic acid (4.4 ml) at 0° C. A solution of 3-[1-(2-aminoethyl)piperidin-4-yl]-5-chloro-1-(4-fluorophenyl)-1H-indole (10.8 g) prepared according to Example 1 in dichloromethane (100 ml) is added dropwise followed by stirring for 6 hours at room temperature. Water (100 ml) is added and the reaction mixture is made alkaline with concentrated ammonia. The phases are separated, followed by extraction with dichloromethane. The combined organic phases are dried over magnesium sulfate. Removal of solvent under vacuum gives a heavy oil which is purified by flash chromatography (silica gel, eluent: triethylamine/methanol/ethyl acetate 5:20:75). About 7.9 g of the title compound is isolated as a crystalline material.

Preparation of 1-[2-[4-[5-Chloro-1-(4-fluorophenyl)-1H-indol-3-yl]piperidin-1-yl]ethyl]4,5-dehydroimidazolidin-2-dione The title compound (dehydro-sertindole) is prepared by reacting one equivalent 5-chloro-1-(4-fluorophenyl)-3-[1-] 2-ureidoethyl)piperidin-4yl]-1H-indol (1.6 g) with one equivalent 1,2-dibromoethylene (Aldrich Chemical Company, Inc., Milwaukee Wis.) under conditions analogous to those provided in U.S. Pat. No. 5,703,087. The resulting product is dried over magnesium sulfate and purified by column chromotography.

5.4. Example 4

Determination of Binding Affinities

The binding affinities of sertindole, 5-oxo-sertindole, nor-sertindole, and dehydro-nor-sertindole were determined at the non-selective $\alpha_1$ receptor from rat cerebral cortex, the human recombinant dopamine ($D_2$ and $D_4$), and serotonin (5-$HT_{2A}$) receptors. Techniques known to those skilled in the art were employed. See, e.g., Greengrass, P. and Bremner, R. *Eur. J. Pharmacol.* 55:323–326 (1979); Leysen, J. E. et al., *Mol. Pharmacol.* 21:301–314 (1982); Terai, M. et al., *Eur. J. Pharamcol.* 173:177–182 (1989); and Van Tol, H. H. M. et al., *Nature*, 358:149–152 (1992). Compounds were initially tested at 10 $\mu$M in duplicate, and if $\geq$50% inhibition of specific binding was observed, they were tested further at 10 different concentrations in duplicate in order to obtain full competition curves.

5.5. Example 5

Binding Affinities

The binding affinities of sertindole, nor-sertindole, 5-oxo-sertindole, and dehydro-nor-sertindole were determined at the nonselective $\alpha_1$ receptor from rat cerebral cortex, and the human recombinant dopamine ($D_2$ and $D_4$) and serotonin (5-$HT_{2A}$) receptors using methods analogous to those of Example 4. Compounds were tested initially at 10 $\mu$M in duplicate, and if $\geq$50% inhibition of specific binding was observed, they were tested further at 10 different concentrations in duplicate in order to obtain full competition curves. $IC_{50}$ values (concentration required to inhibit 50% specific binding) were then determined by nonlinear regression analysis of the curves and are shown with calculated inhibition constants ($K_i$) in Table 1 below.

TABLE 1

| Compound | $IC_{50}$ ($K_i$) by Receptor | | | | $5\text{-HT}_{2A}$ Selectivity |
|---|---|---|---|---|---|
| | $\alpha_1$ | $D_2$ | $D_4$ | $5\text{-HT}_{2A}$ | ($D_2/5\text{-HT}_{2A}$) |
| Sertindole | 6.2 | 21 | 80 | 11 | 1.9 |
| | (1.7) | (5.4) | (24) | (7.0) | |
| 5-Oxo | 12 | 44 | 315 | 18 | 2.4 |
| | (3.3) | (11) | (96) | (11) | |
| Nor | 49 | 78 | 1,090 | 17 | 4.6 |
| | (13) | (20) | (333) | (11) | |
| Dehydro-Nor | 102 | 34 | 379 | 25 | 1.4 |
| | (28) | (8.8) | (116) | (16) | |
| Prazosin | 0.32 | — | — | — | — |
| | (0.087) | | | | |
| (+)-Butaclamol | — | 11 | — | — | — |
| | | (2.9) | | | |
| Clozapine | — | — | 103 | — | — |
| | | | (31) | | |
| Ketanserin | — | — | — | 2.6 | — |
| | | | | (1.7) | |

"—" = not determined.

It is readily apparent from the data provided in Table 1 that the compounds of the invention (i.e., sertindole derivatives) bind to dopamine ($D_2$ and $D_4$) and serotonin ($5HT_{2A}$) receptors, yet exhibit less affinity for $\alpha_1$-adrenergic receptors than does sertindole. Further, nor-sertindole and 5-oxo-sertindole exhibit greater selectivity for $5\text{-HT}_{2A}$ receptors than for $D_2$ receptors.

5.6. Example 6

Inhibition of Withdrawal Symptoms

The effect of a sertindole derivative on the relief of substance withdrawal in mice is measured as the effect on some specific behavioral changes following withdrawal of the substance. Such an animal model has been shown to be indicative of effects on withdrawal symptoms. See, e.g., Barry et al., *Pharmac. Biochem. Behav.* 27:239–245 and Costall et al., *Pharmac. Biochem. Behav.* 33:197 (1989).

The mice (preferably male BKW mice weighing about 25–30 g) are housed in groups of 10 and given free access to drink and food and kept on a dark/light cycle of 12 hours. The test is conducted using an open-top experimental box (45×27×27 cm) two fifths of which is partitioned from the rest, painted black and illuminated with a dim red light (1×60 W, zero Lux). The remainder of the box is painted white and brightly illuminated (60 W, 400 Lux) with a white light source. The light sources are located 17 cm above the box and the base of the box is lined into 9 cm squares. Access between the two compartments is by means of a 7.5×7.5 cm opening located in floor level at the center of the partition.

Following administration of diazepam, nicotine, cocaine, or alcohol as indicated below, the test is carried out by taking the mice to a dimly illuminated room and then, after one hour adaptation to the new environment, placing them in the center of the white section of the test box. Withdrawal, which is indicated by a significant preference for the black section of the box, is evaluated by remote video recording and includes: a) the time spent in the white and black section; b) the number of explorative rearings in both the white and black section; c) the number of line crossings in the white and black section; and d) the latency of the initial movement from the white to the black area. Separate groups of mice are used for each behavioral assessment and the experiment is carried out blind.

Diazepam Withdrawal

Diazepam (10 mg/kg) is given i.p. twice a day for 7 days and then withdrawn. At the time of the last dose the mice receive the test substance (e.g., sertindole derivative), and on the following day receive a dose of test substance in the morning than then again about 40 minutes prior to testing.

Nicotine Withdrawal

Nicotine is given (0.1 mg/kg i.p., b.d) for 7 days and test compound is given with the last dose of nicotine. Animals are tested on the day after receiving a total of 3 doses of test compound (e.g., sertindole derivative).

Cocaine Withdrawal

Cocaine is given (1 mg/kg i.p., b.d) for 14 days and test compound is given during withdrawal for 24 hours (i.p., b.d).

Alcohol Withdrawal

Alcohol is given for 14 days (8% in drinking water) and withdrawn for 24 hours. Test compound is given during withdrawal (i.p., b.d).

5.7. Example 7

Inhibition of Memory Impairment

The ability of the compounds of the invention (i.e., sertindole derivatives and pharmaceutically acceptable salts, solvates, and clathrates thereof) to treat or prevent memory impairment may be determined from their ability to inhibit scopolamine induced memory impairment in mice. In this test, the effect of a sertindole derivative on mouse movement from an aversive white brightly illuminated compartment to a less aversive black dimly illuminated compartment while under the effect of scopolamine is determined.

The test is conducted using an open-top experimental box (45×27×27 cm) two fifths of which is partitioned from the rest, painted black and illuminated with a dim red light (1×60 W, zero Lux). The remainder of the box is painted white and brightly illuminated (60 W, 400 Lux) with a white light source. The light sources are located 17 cm above the box and the base of the box is lined into 9 cm squares. Access between the two compartments is by means of a 7.5×7.5 cm opening located in floor level at the center of the partition.

The mice (preferably aged male albino BKW mice of between 8 and 12 months) are housed in groups of 10 and given free access to drink and food and kept on a dark/light cycle of 12 hours.

The test is carried out by placing the mice (taken from a dark home environment) in the center of the white section of the test box. The test period is 5 minutes per day. The latency to move from the white to the black section is assessed via remote video recording. On day four, scopolamine (0.25 mg/kg i.p., b.d, for a control group of young mice or 0.1 mg/kg for the test or control aged mice) is given 40 minutes prior to testing. The latency to enter the black section decreases with repeated testing. However, the latency increases following the administration of scopolamine. Cognition enhancers block the latency increase produced by scopalamine. Data obtained are analyzed by a one-way ANOVA followed by Dunnett's t-test.

5.8. Example 8

Oral Formulations

Preferred individual dosage forms of the compounds of the invention (i.e., sertindole derivatives and pharmaceutically acceptable salts, solvates, and clathrates thereof) are suitable for oral administration. Examples of such preferred dosage forms are provided below.

5.8.1 Example 8.1

Tablet Dosage Forms

Table 2 provides the ingredients for a tablet dosage form of sertindole derivative:

TABLE 2

| Component | Quantity per Tablet (mg) |
| --- | --- |
| Sertindole derivative | 75 |
| Lactose | 125 |
| Corn Starch | 5.0 |
| Water (per thousand tablets) | 30.0 ml * |
| Magnesium Stearate | 0.5 |

* The water evaporates during manufacture.

The active ingredient (i.e., a sertindole derivative or pharmaceutically acceptable salt, solvate, or clathrate thereof) is blended with the lactose until a uniform blend is formed. The smaller quantity of corn starch is blended with a suitable quantity of water to form a corn starch paste. This is then mixed with the uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets are coated by standard aqueous or nonaqueous techniques.

Another tablet dosage formulation suitable for use with the active ingredient of the invention is provided by Table 3:

TABLE 3

| | Quantity per Tablet (mg) | | |
| --- | --- | --- | --- |
| Component | Formula A | Formula B | Formula C |
| Sertindole derivative | 20 | 40 | 100 |
| Lactose BP | 134.5 | 114.5 | 309.0 |
| Starch BP | 30 | 30 | 60 |
| Pregelatinized Maize Starch BP | 15 | 15 | 30 |
| Magnesium Stearate | 0.5 | 0.5 | 1.0 |
| Compression Weight | 200 | 200 | 500 |

The active ingredient is sieved and blended with lactose, starch, and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to pharmaceutically acceptable carrier, the compression weight, or by using different punches.

5.8.2 Example 8.2

Capsule Dosage Forms

Capsules of sertindole derivative suitable for use in the treatment of neuroleptic and related disorders are made using the ingredients provided in Table 4:

TABLE 4

| | | Quantity per Capsule (mg) | | |
| --- | --- | --- | --- | --- |
| Formulation | | A | B | C |
| Ingredients | Sertindole derivative | 50.0 | 100.0 | 200.0 |
| | Lactose | 48.5 | 148.5 | 48.5 |
| | Titanium Dioxide | 0.5 | 0.5 | 0.5 |
| | Magnesium Stearate | 1.0 | 1.0 | 1.0 |
| Fill Weight | | 100.0 | 250.0 | 250.0 |

The active ingredient (i.e., a sertindole derivative or a pharmaceutically acceptable salt, solvate, or clathrate thereof) is sieved and blended with the excipients. The mixture is filled into suitably sized two-piece hard gelatin capsules using suitable machinery. Other doses may be prepared by altering the ratio of Sertindole derivative and pharmaceutically acceptable carrier, the fill weight and, if necessary, by changing the capsule size to suit.

The embodiments of the invention described above are intended to be merely exemplary, and those skilled in the art will recognize, or be able to ascertain using no more than routine experimentation, numerous equivalents to the specific procedures described herein. All such equivalents are considered to be within the scope of the invention and are encompassed by the following claims.

What is claimed is:

1. A method of treating or preventing a neuroleptic or related disorder while reducing or avoiding adverse effects associated with the administration of sertindole, which comprises administering to a human in need of such treatment or prevention a therapeutically effective amount of a sertindole derivative, wherein the sertindole derivative is nor-sertindole, 5-oxo-sertindole, dehydro-sertindble, dehydro-nor-sertindole, or a pharmaceutically acceptable salt, solvate, hydrate, or clathrate thereof.

2. The method of claim 1 which further comprises the reduction or avoidance of adverse effects associated with antagonism of $\alpha_1$-adrenergic receptors.

3. The method of claim 1 wherein the adverse effect is QT prolongation.

4. The method of claim 1 wherein the sertindole derivative is dehydro-nor-sertindole.

5. The method of claim 1 wherein the neuroleptic or related disorder is selected from the group consisting of psychosis, depression, anxiety, substance addiction, memory impairment and pain.

6. The method of claim 5 wherein the neuroleptic or related disorder is psychosis.

7. The method of claim 6 wherein the psychosis is selected from the group consisting of hallucinations, paranoia, affective psychosis, alcoholic psychoses, arteriosclerotic psychosis, amnestic psychosis, bipolar psychosis, Cheyne-Stokes psychosis, climacteric psychosis, depressive psychosis, drug psychosis, dysmnesic psychosis, hysterical psychosis, infection-exhaustion psychosis, Korsakoff's psychosis, postinfectious psychosis, postpartum psychosis, posttraumatic psychosis, senile psychosis, situational psychosis, toxic psychosis, traumatic psychosis, Windigo psychosis, schizo-affective psychosis and schizophrenia.

8. The method of claim 7 wherein the psychosis is schizophrenia.

9. The method of claim 6 which further comprises the adjunctive administration of an atypical antipsychotic, or a pharmaceutically acceptable salt, solvate or clathrate thereof.

10. The method of claim 9 wherein the atypical antipsychotic is mirtazapine.

11. The method of claim 5 wherein the substance addiction is addiction to a substance selected from the group consisting of central nervous system depressants, anxiolytics, stimulants, and hallucinogens.

12. The method of claim 11 wherein the central nervous system depressant is selected from the group consisting of alcohol, barbiturates, ethchlorvynol, glutethimide, methaqualone, methyprylon and natural and synthetic opiates.

13. The method of claim 11 wherein the anxiolytic is selected from the group consisting of alprazolam, oxazepam, temazepam, chlordiazepoxide and diazepam.

14. The method of claim 11 wherein the stimulant is selected from the group consisting of amphetamines, nicotine and cocaine.

15. The method of claim 5 wherein the neuroleptic or related disorder is pain.

16. The method of claim 15 wherein the pain is selected from the group consisting of acute, chronic, somatogenic and psychogenic pain.

17. The method of claim 16 wherein the somatogenic pain is neuropathic pain.

18. The method of claim 17 which further comprises the adjunctive administration of a therapeutic agent selected from the group consisting of opiate analgesics, non-opiate analgesics, antipyretics, nonsteroidal anti-inflammatory drugs, tricyclic antidepressants, serotonin reuptake inhibitors, mixed serotonin-norepinephrine reuptake inhibitors, serotonin receptor agonists, cholinergic analgesics, adrenergic agents, neurokinin antagonists, and xanthine oxidase inhibitors and pharmaceutically acceptable salts, solvates, hydrates and clathrates thereof.

19. The method of claim 18 wherein the tricyclic antidepressant is selected-from the group consisting of desipramine, imipramine, amytriptiline and nortriptile.

20. The method of claim 18 wherein the serotonin reuptake inhibitor is selected from the group consisting of fluoxetine, paraoxetine, sertraline and methysergide.

21. The method of claim 18 wherein the mixed serotonin-norepinephrine reuptake inhibitor is selected from the group consisting of venlafaxine and duloxetine.

22. The method of claim 18 wherein the cholinergic analgesic is selected from the group consisting of ketoprofen, aspirin, acetominophen, indomethacin, ketorolac and methotrimeprazine.

23. The method of claim 18 wherein the xanthine oxidase inhibitor is allopurinol.

24. The method of claim 1, wherein the human is younger than about 14 years of age.

25. The method of claim 1, wherein the human is older than about 60 years of age.

26. The method of claim 25, wherein the human suffers from senile dementia or another age-related cognitive disorders.

27. The method of claim 1, wherein the human is at risk of hypertension heart failure and/or arrhythmia.

28. The method of claim 27, wherein the human is obese.

29. The method of claim 28, wherein the human smokes or used to smoke tobacco.

30. The method of claim 1, wherein the human has cardiovascular disease.

31. The method of claim 1, wherein the human is undergoing therapy for high blood pressure, heart disease and/or arrhythmia.

32. The method of claim 1, wherein the human is currently taking an $\alpha_1$-adrenergic receptor antagonist.

33. The method of claim 1 wherein the therapeutically effective amount of sertindole derivative is from about 0.1 to about 1000 mg per day.

34. The method of claim 33 wherein the therapeutically effective amount of sertindole derivative is from about 5 to about 500 mg per day.

35. The method of claim 34 wherein the therapeutically effective amount of sertindole derivative is from about 10 to about 200 mg per day.

36. The method of claim 1 wherein said sertindole derivative, or pharmaceutically acceptable salt, solvate, hydrate, or clathrate thereof, is administered to the patient orally, mucosally, parenterally, sublingually, transdermally, buccally, or topically.

37. The method of claim 36 wherein said sertindole derivative, or pharmaceutically acceptable salt, solvate, hydrate, or clathrate thereof, is administered to the patient orally.

* * * * *